United States Patent [19]

Chae et al.

[11] 4,274,744
[45] Jun. 23, 1981

[54] DIRECT READING DIGITAL COLORIMETER

[75] Inventors: Charles H. Chae, Greenfield; Donald E. Black; Ramesh M. Shah, both of Indianapolis, all of Ind.

[73] Assignee: Medico Electronic, Inc., Indianapolis, Ind.

[21] Appl. No.: 962,682

[22] Filed: Nov. 21, 1978

[51] Int. Cl.$^3$ ............................................. G01N 21/27
[52] U.S. Cl. .................................................... 356/414
[58] Field of Search ........................................ 356/414

[56] References Cited

U.S. PATENT DOCUMENTS

| | | | |
|---|---|---|---|
| Re. 21,907 | 9/1941 | Balsley | 250/205 |
| 3,833,864 | 9/1974 | Keiss et al. | 356/414 |

*Primary Examiner*—John K. Corbin
*Assistant Examiner*—Bruce Y. Arnold
*Attorney, Agent, or Firm*—Fisher, Christen & Sabol

[57] ABSTRACT

A new colorimeter blood analyzer having a capacity of simultaneously performing a specific blood test and reading the prothrombin time on a separate digital readout device. The program circuit module with appropriate calibration parameters which is self-referencing performs specific tests providing direct display of the desired blood constituent concentration. The analyzer provides an independent prothrombin well having a separate optical source for prothrombin time measurement providing direct display on an independent readout display. The analyzer also has a built-in digital readout quartz crystal timing device which can be operated when prothrombin time analysis is not conducted. The entire analyzer is contained in a compact console which includes controlled incubated storage for blood test samples together with insertion cavities for both constituent concentration and prothrombin time analysis. The results of each analysis are so normalized by the blood analyzer that a numerical readout is presentable on an independent readout device and these results are substantially instantaneously displayed subsequent to initiation of any given test in the analyzer. A control circuit for the tungsten filament lamp used in the chemical analyses increases the useful life of the lamp by limiting the amount of time that the lamp is operated at its highest voltage.

10 Claims, 4 Drawing Figures

DIRECT READING DIGITAL COLORIMETER

REFERENCE TO PRIOR PATENTS

This invention relates to an improvement over the inventions disclosed and claimed in U.S. Pat. Nos. 3,819,276 and 3,833,864, issued to Kiess et al June 25, and Sept. 3, 1974, respectively, and owned by the assignee of the present application.

DESCRIPTION OF THE PRIOR ART

Said prior applications disclosed a small console type colorimeter capable of performing a number of colorimetric tests for determining the various constituents of blood samples as well as the prothrombin time of a blood sample.

In said prior apparatus a temperature controlled incubator is provided to receive a series of cuvettes containing individual blood samples and reagent prior to colorimeter analysis. A test well is also provided which is disposed in the path of radiant energy supplied by an intensity-controlled light source. In addition a series of light filters are mounted on a wheel to be selectively moved into the light path by a servo motor, in accordance with the particular test to be performed.

The intensity of the filtered light transmitted through the cuvette containing the sample is detected by a sensor whose output is fed to a computing circuit including an analog-to-digital converter which then energizes a conventional L.E.D. digital display to provide an indication of the particular constituent present in the sample in appropriate terms, such as percentage, weight or volume, or other measurement.

Space is provided in the console for a series of replaceable insertable modules, each of which corresponds to a particular blood analysis to be made. Each module includes several components of the aforementioned computing circuit, the values of which are adjusted in each case to establish the correct parameters of the computing circuit suitable for the corresponding test to be performed, including the proper electrical value for setting the proper filter in the light path, and a series of pushbutton switches are arranged on the console for connecting a selected module into the circuit.

In the prior machine both chemical analyses and prothrombin time test take place by inserting the sample in a cuvette into a single well which is irradiated by a light source having a regulated intensity, but a separate light responsive sensor is used to measure the intensity of light from a cuvette containing a blood sample for a prothrombin test. Also, a separate digital readout from that used to display the results of the chemical analysis is utilized to display the prothrombin time test results.

SUMMARY OF THE INVENTION

This invention is an improvement over the colorimeter described and claimed in the previously mentioned Kiess et al patents in that, while the constituent concentration analyses and prothrombin tests may utilize the same electrical circuitry as employed in the past, the controls for the various elements and components have been altered and rearranged to vastly expand the variety of analyses that can be performed and to increase the ease with which these capabilities can be utilized.

One example is the fact that the controls for the selection of filters, placement of the decimal in the digital display and high and low factors (slope and reagent blank) of the computing circuit have been placed on the control panel of the console so that the user can select each of these factors individually and thus, theoretically condition the apparatus to perform an unlimited variety of chemical analyses, including those which may be developed in the future.

Another object of the invention is to provide in addition a certain number of pre-programmed tests, each of which can be selected by actuating a single pushbutton as in the case of the previously known apparatus. These pushbutton controls are interlocked with another pushbutton which enables the user to alternate between the pre-programmed and the manually selectable modes of operation.

The invention also includes a light source, separate from the filtered light source, and a separate digital readout for conducting a prothrombin time test concurrently with a constituent concentration analyses. The time tests are automatically initiated by insertion of a cuvette which contains prothrombin reagents into a well which is separate from the well for chemical analyses.

Another object is to provide an additional manually settable circuit for utilizing the separate prothrombin time readout for measuring elapsed time; an arrangement which obviates the necessity for an additional timer for conducting chemical analyses, or other wholly unrelated tasks.

DESCRIPTION OF THE PREFERRED EMBODIMENT

Figure 1:
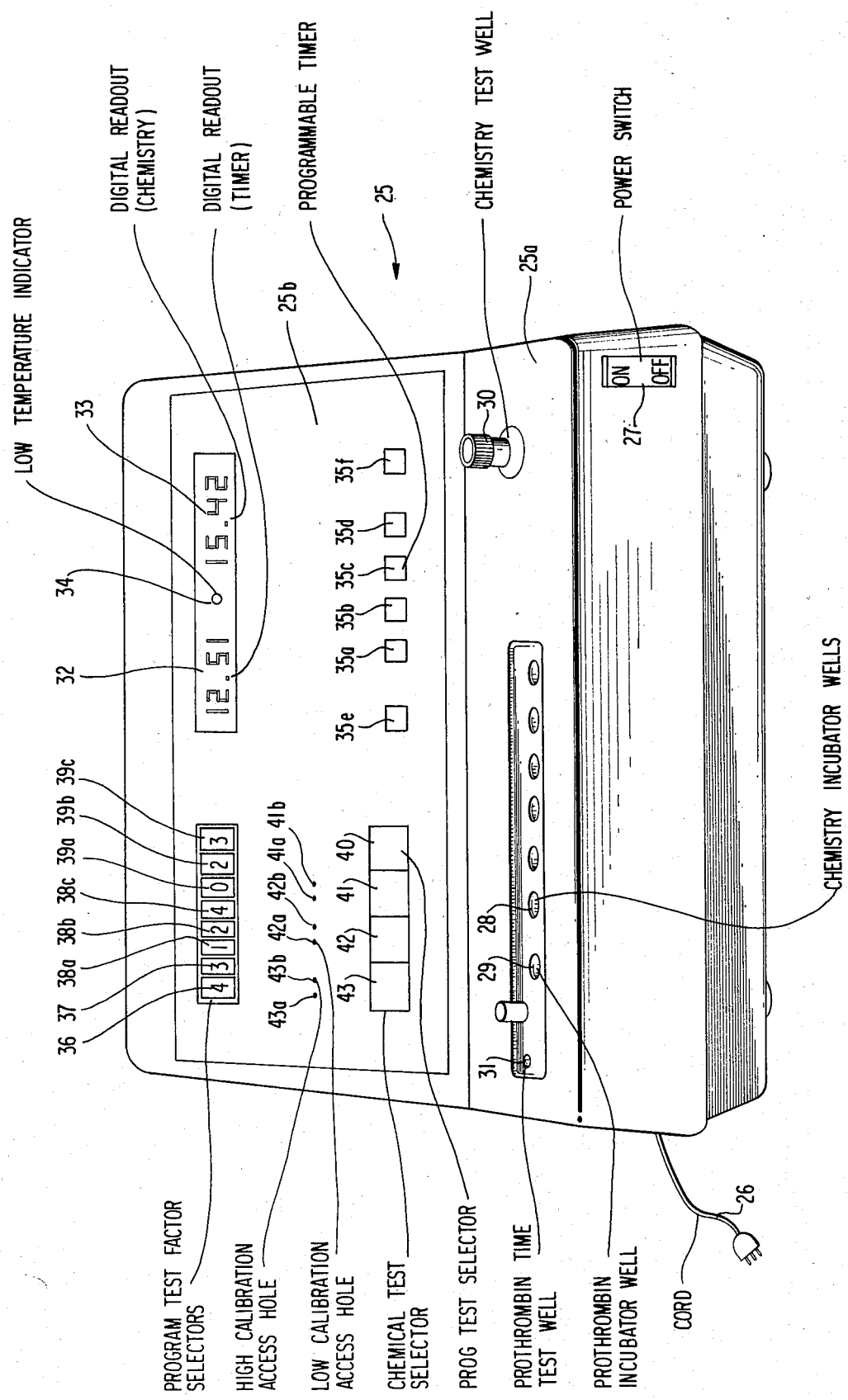
FIG. 1 is a perspective view of a console containing a preferred form of direct reading digital colorimeter in accordance with this invention.

Referring now to the drawings in detail, in FIG. 1 there is shown a portable console, indicated generally by numeral 25, having a horizontal forward working surface 25a and a sloping panel 25b. A line cord 26 may be plugged into the usual electrical outlet to supply energy to the components within the console under the control of a power switch 27 which includes a resettable circuit breaker to protect against overloads.

To the left of the front surface there is an opening which exposes the upper surface of an incubator containing a number of wells 28 for cuvettes containing samples for chemical analysis and several wells 29 for cuvettes containing samples for prothrombin tests. To the right there is an opening to expose a well 30 containing a holder for a cuvette containing a sample for chemical analysis, while a similar well 31 for prothrombin tests is provided at the left.

At the upper left of the sloping panel a four unit LED numerical readout 32 displays selectively either elapsed time or prothrombin time while a 3½ unit readout 33, having a movable decimal, displays constituent concentrations in terms of percentage or other values as called for in a particular chemical analysis. Between the readouts is a visual signal 34 actuated by low incubator temperature. Below the readouts are a series of pushbuttons which control switches for controlling readout 32 when used as a timer. Pushbuttons 35a and 25b set the tens and units of minutes, respectively, and buttons 35c and 35d, respectively set the tens and units of seconds on the timer in the usual way by depressing them until the desired elapsed time is displayed. This time is then entered in the memory circuit by depressing Reset button 35e. Although, when using the timer for prothrombin testing, it is started by a cuvette which contains reagent in well 31, when it is used independently it can be actuated by pushbutton 35f to count the time entered by Reset button 35e; at the end of the cycle an audible alarm "beep" is actuated.

At the upper left of the panel are a series of rotary thumbwheel switches mounted in horizontal alignment for individual manual rotation about a common horizontal axis, each of them bearing numerals from "1" to "0" indicating ten angular switching positions. These switches enable the operator to program various components of the system to perform any one of a number of chemical constituent analysis. These switches enable the performance of at least twenty different types of analysis of blood samples according to parameters which have already been established and, in addition, as other analyses become useful, they may be programmed in by proper settings of these thumbwheel switches.

Rotary switch 36 selects the particular filter to be used for a particular test. Since there are only five filters presently used, only the 1—5 positions are used to insert values of resistance into the servomotor control circuit for the filter wheel in a manner similar to the changing of resistance RS in the modules of the prior Kiess et al patents. Rotary switch 37 selects the placement of the decimal in readout 33 by energizing the decimal at the desired location. At position "1" the decimal is elminated so that the display reads in whole numbers. Position "2" sets the decimal to read in tenths and at position "3" the display reads the hundredths. The other positions on this switch are not used.

The thumbwheels 38a, 38b and 38c regulate the values of three variable resistors in the manner of a decade box to insert a value of resistance into the computing circuit to provide the correct reagent blank ratio in the log-amplifier. The thumbwheels 39a, 39b and 39c regulate another group of decade box resisters to provide the correct resistance value for the slope function circuit by controlling the input resistance in the log-amplifier. These functions are described in detail in the earlier Kiess et al U.S. Pat. No. 3,819,276 in connection with resisters R2 and RC.

On the sloping panel, below the thumbwheels are a series of interlocked pushbuttons 40, 41, 42 and 43 provided with means for receiving a changeable identifying indicia. Each button also includes a small interior lamp which is lit when the button is depressed and the button and indicia may be translucent to allow ready identification when placed in the depressed position. Pushbutton 40 actuates switch means which connects the programable thumbwheel elements 36, 37, 38a, 38b, and 38c and 39a, 39b, and 39c into their respective circuits while each of the pushbuttons 41, 42 and 43, by releasing the program switch 40 (or any of the other of the adjacent pushbuttons) disconnects the components controlled by elements 36, 37, 38a, 38b and 38c and 39a, 39b and 39c from their respective circuits and inserts other corresponding components which have been set to predetermined values in their place to perform a specific one of a number of chemical constituent analyses. Above each of the buttons 41, 42 and 43, there are a pair of access openings 41a, 41b, 42a, 42b, 43a and 43b and on the back of the panel there are mounted suitable variable resisters for adjusting the pre-set values, by means of a suitable tool, of the respective values of reagent blank values, in the case of openings 41a, 42a and 43a and the respective slope functions, in the case of openings 41b, 42b and 43b.

Figure 2:
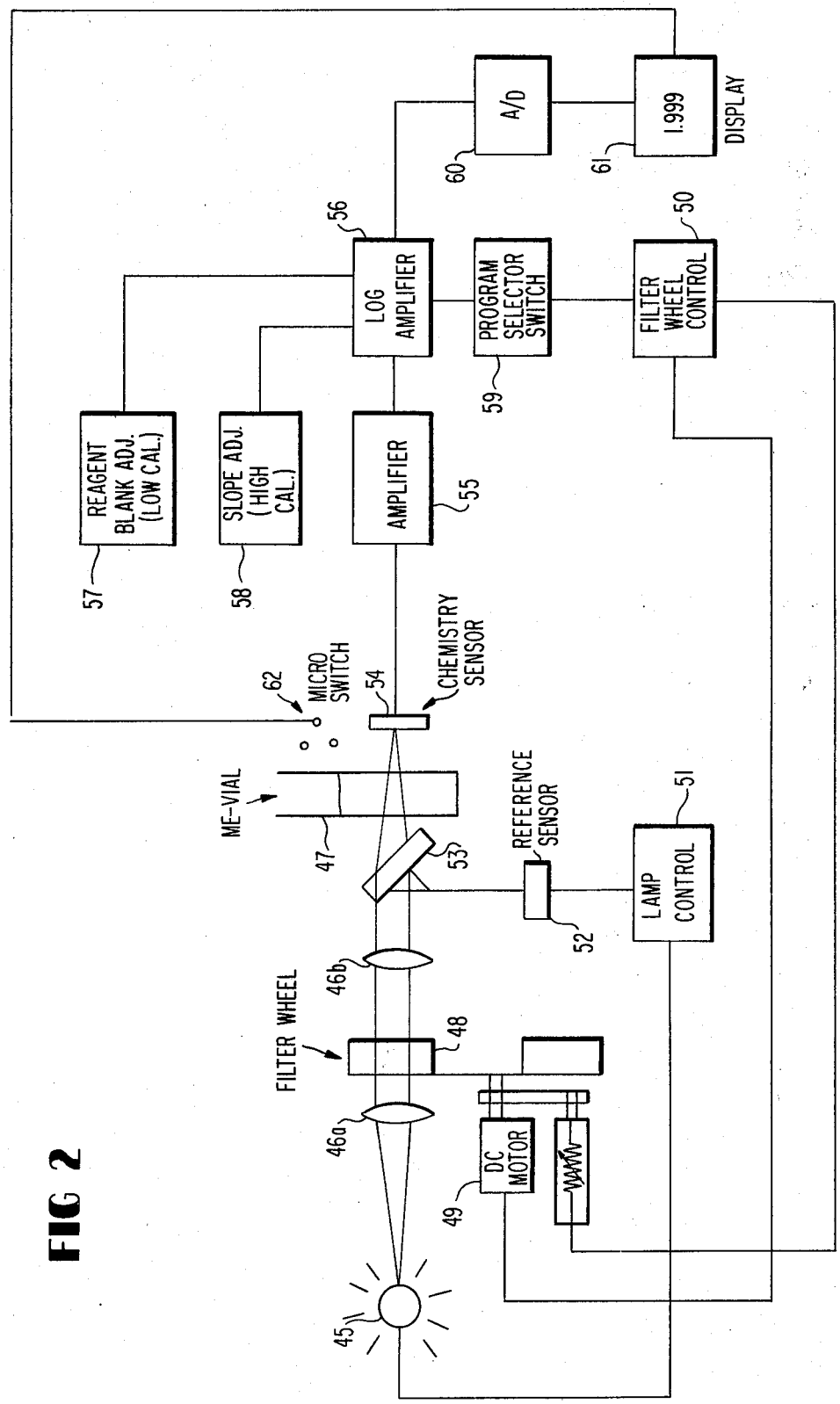
FIG. 2 is a block diagram of the chemical constituent analysis components.

In FIG. 2 there is shown a schematic arrangement of the mechanical elements and block diagrams of the circuitry for chemical analyses. An incandescent lamp 45 is the light source whose beams are focused by lens 46a and 46b to concentrate on a cuvette 47 inserted in the well 30. Between the lenses is a wheel 48 containing, for example, five filters for passing different ranges of light. The filter wheel is rotatably positioned by a motor 49 under control of either the pre-programmed pushbuttons 41, 42, 43 or the manual switch 36 in the control circuit 50. The intensity of the lamp is controlled through a circuit 51 which is responsive to a sensor 52 which is aligned to receive a portion of the light through a beam splitter 53. Another light sensor 54 receives light from the cuvette 47 and feeds a signal to the converter and amplifier circuit 55 which, in turn, feeds a log amplifier computing circuit means 56. The reagent blank adjustment (low calibration) circuit 57 includes the controls 38a, 38b and 38c on the console and adjustments 41a, 42a and 43a for the pre-programmed analyses. The slope adjustment (high calibration) 58 includes controls 39a, 39b and 39c and adjustments 41b, 42b and 43b. The program selector circuit 59 includes the pushbuttons 40, 41, 42 and 43 on the control panel. The output of the log amplifier 56 goes to the analog-digital converter circuit 60 which may include an integrated cirucit manufactured by Intersel and identified as No. 7107. The digital display 61 is controlled by converter 60 and is energized by a microswitch 62 which is actuated by contact with a cuvette 47 when inserted in the well.

Figure 3:
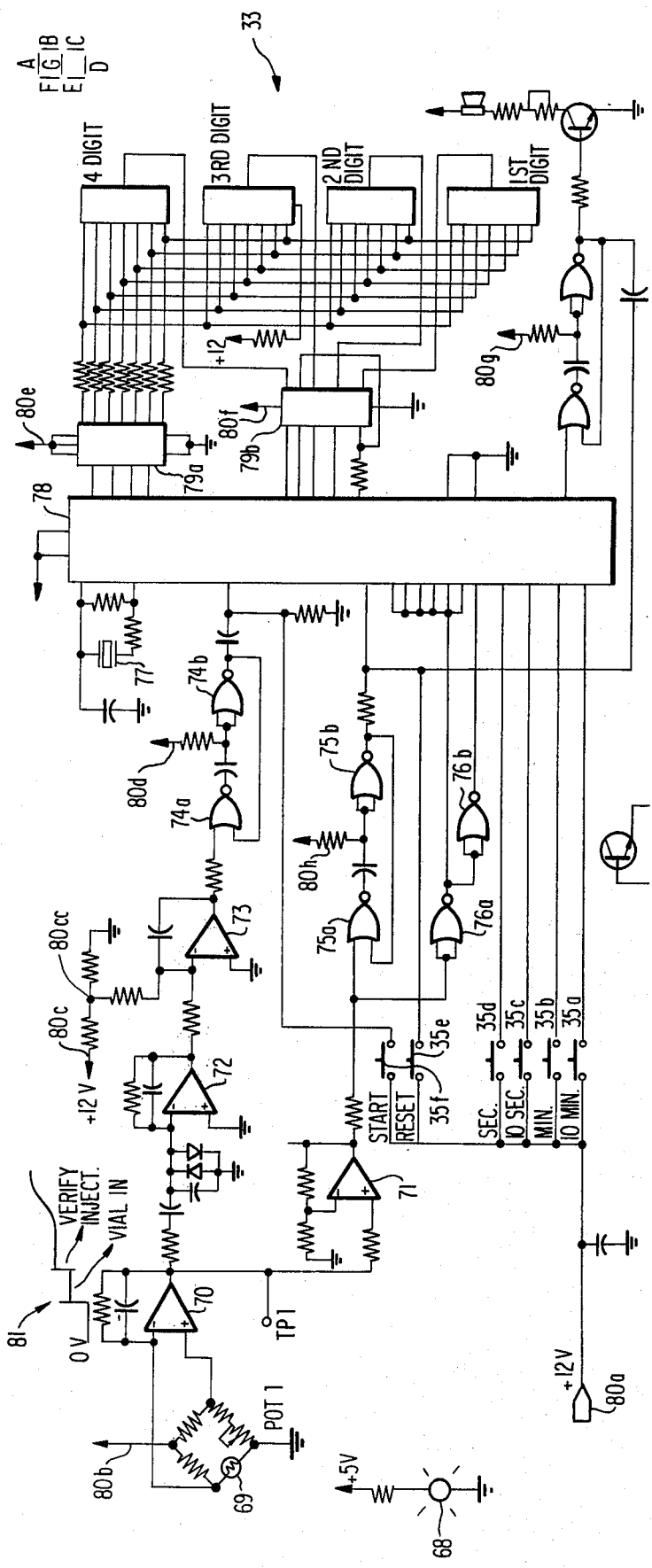
FIG. 3 is a diagram of one form of circuit for determining prothrombin time.

The prothrombin time testing circuit, combined with the selective timer cirucit is shown in FIG. 3; and includes a light source 68, light sensor 69, first and second amplifiers 70 and 71, a differentiator 72, comparator 73, gates 74a and 74b, gates 75a and 75b gates 76a and 76b, quartz crystal 77 cut to resonate at 32.78 KH, and integrated counting circuit 78 manufactured by National Semiconductor Corp. and identified by catalog number MM5865, a pair of decoding circuits 79a and 79b and, finally the 4 digit display 32 (shown in FIG. 1).

With the exception of the light source 68, which is a tungsten filament lamp fed from a 5-volt source, the timing circuit is connected at 80a, 80b, 80c, 80d, 80e, 80f, 80g and 80h to a 12 volt regulated DC supply (not shown).

The lamp 68 is energized at all times to illuminate the well 31 (FIG. 1) at all times but this well is made of black anodized aluminum so that in the absence of a cuvette, the diffused light is at a minimum. The sensor 69 is placed in the well at right angles to the path of light from source 68 so that when a cuvette is first inserted there is a slight increase in the diffused light, as indicated by the small graph 81, which will change the output of amplififer 70 from −5 v. to +5 v. This change, differentiated by differentiator 72 is compared by comparator 73 with the voltage of +1.5 supplied from the resistance tap 80cc and triggers a "one shot" circuit comprising gates 74a and 75b. The width of this pulse is 4 seconds but, at the same time, amplifier 71 has been saturated to trigger the other "one shot" circuit comprising gates 75a and 75b, to produce a 5 second pulse which overrrides the first pulse to reset the counting circuit of integrated circuit 78. When the output of amplifier 71 is in a High state (Logic "1") the gate 76a will cause the circuit 78 to count in 1/100 second increments, and the second digit (a divide-by-10 counter output) will be displayed at 33. When the amplifier 71 output is switched Low (Logic "0") the gate 76b will cause the clock circuit to count in one second increments and the second digit is divided by a 6-count so that every 60 seconds the display 33 will be advanced by one minute. When serum is injected into the inserted cuvette it will interrupt the light level to generate a pulse to start the clock counting sequence. While the clotting is in progress, the light level will keep increasing until it reaches a certain level, at which time the comparator 73 goes to a positive position to trigger the "one shot" 74a and 74b to stop the clock counting. While the actual count of the timing circuit is in 1/100 second increments and the actual display, when the cuvette is removed, is in hundredths of a second, the hundreths' digit is of insignificant value.

The manual controls for the timer 35a, 35b, 35c, 35d, 35e and 35f, shown on the console panel in FIG. 1, are also identified in the circuit of FIG. 3.

While the electrical system varies in some respects from the prior Kiess et al U.S. Pat. Nos. 3,819,276 and 3,833,864 in some respects, it should be understood that the disclosures embodied in those patents can be adapted for use in the present invention and they are incorporated herein by reference. A primary aspect of the present invention is the repositioning of the controls of said earlier circuits in such a way as to increase their versatility. As an example, but not a limiting one, by making the blank reagent and slope resister circuits capable of almost infinite and adjustment by the user, it is possible to program the appratus for improved types of the present chemical analyses, as well as other types of analyses not yet developed.

OPERATION OF THE CALIBRATING SYSTEM

The use of this apparatus is coordinated with chemical reagents for each type of chemical analysis, the chemicals being normally supplied in the form of packages, or kits, containing a quantity of vials, or cuvettes, each containing reagents for a single analysis. In addition, there is furnished with each kit a Control Number containing eight digits and a package insert which includes instructions for the preparation of a reagent blank calibration vial and a test vial (slope calibration). The insert will also contain the setting for the proper light filter and the decimal placement of the readout.

The Control Number is not essential, but it serves to provide an approximate setting of the thumbwheels 36, 37, 38a, 38b, 38c (the blank reagent setting) and 39a, 39b and 39c (slope setting). Of course, the setting of thumbwheel 36 causes the servomotor to place the proper filter in the light path focussed on well 30, and thumbwheel 37 selects the position for the decimal in readout 33. When the apparatus has been turned on, the blank reagent setting can usually be obtained by inserting the reagent vial supplied with the kit into the well and adjusting the thumbwheels 38a, 38b and 38c until the readout 33 indicates "000". In some cases additional treatment, including the addition of measured quantities of one or more chemicals to the reagent in the vial supplied with the kit will be required, according to instructions in the insert.

It is also necessary to prepare a test vial to calibrate the slope factor, and instructions are supplied in the insert for this purpose. It is also possible to obtain test vials for this purpose commercially supplied by many other Companies. When the test vial is substituted in the well 30, the thumbwheels 39a, 39b and 39c are adjusted to obtain the display of a number on readout 33 which will vary from one type of analysis to another. This number is supplied with the package insert, or is contained in an instruction manual accompanying the machine.

Calibration of the programmed analyses set up by pushbuttons 41–43 is not often required, although a check of the calibration should be made at regular intervals, or from batch to batch of reagent kits obtained. The calibration of these analyses is performed by using a reagent blank vial and adjusting the appropriate resister by inserting a tool through the adjacent opening 41a, 42a or 43a. The slope in each case is obtained with the appropriate test vial and adjustment of the appropriate resister reached through opening 41b, 42b or 43b.

CONTROL CIRCUIT FOR THE CHEMICAL ANALYSIS LIGHT SOURCE

Figure 4:
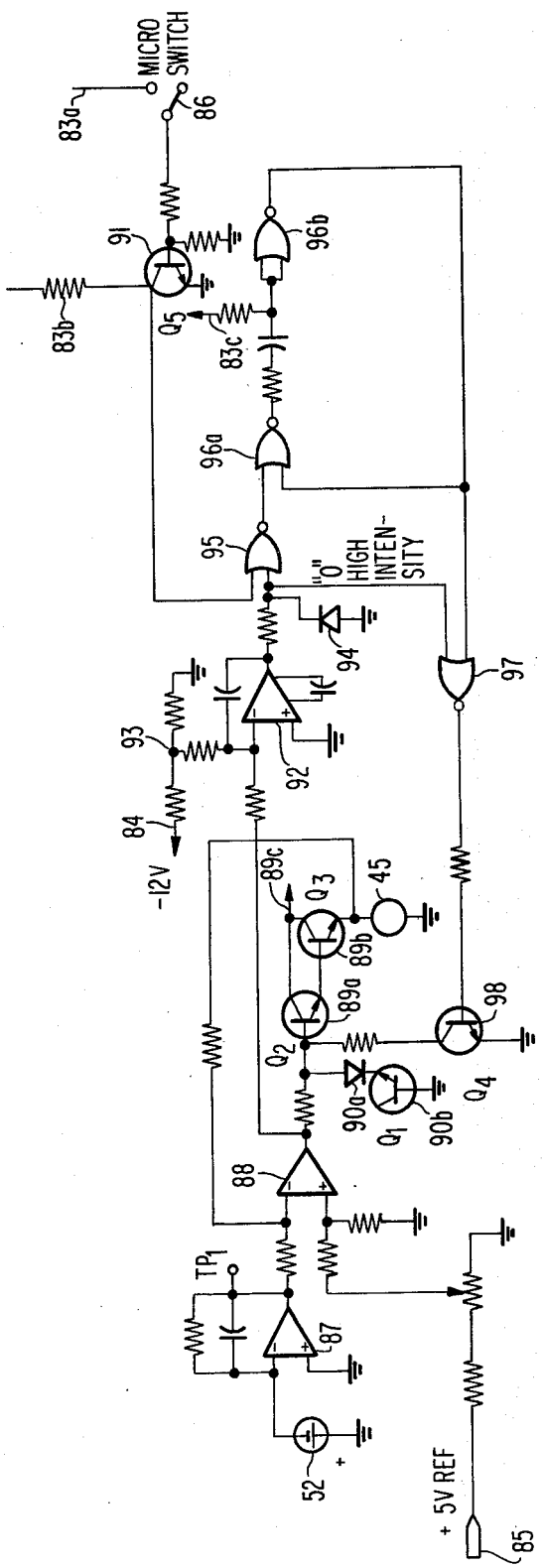
FIG. 4 is a circuit diagram of a control circuit for the light source used in making chemical constituent analyses.

The lamp control circuit, identified in FIG. 2 by numeral 51, is shown in detail in FIG. 4. This circuit is connected at 83a, 83b and 83c to a plus 12 volt DC supply, at 84 to a minus 12 volt DC supply, and at 85 to a plus 5 volt DC closely-regulated supply. The circuit includes a normally open microswitch 86 which is positioned near the bottom of well 30 (FIG. 1) in such a way that it is closed by contact with a cuvette inserted into the well.

The reference sensor 52, and the chemistry sensor 54 (see FIG. 2) are closely matched silicon photo cells which produce proportional currents, and sensor 52, which receives approximately 10% of the transmitted light from beam splitter 53 is enabled by the circuit of FIG. 4 to ensure that the intensity of light from source 45 after passing through any one of the filters mounted on wheel 48, will remain constant. Thus, in the absence of a cuvette in the well 47, the output of chemistry sensor 54 will also assume a constant value.

As soon as the main power 27 (FIG. 1) is turned "on" the filament of lamp 45 will be energized at a level which is sufficiently low to provide long life without the necessity for frequent replacement. Referring to FIG. 4, the output of sensor 52 feeds amplifier 87 which converts the current to a voltage input to comparator 88 which, in turn, regulates the voltage supplied to lamp 45 through transisters 89a and 89b, arranged in the well-known "Darlington Pair" circuit and supplied at 89c from an plus 8.2 volt DC unregulated supply. A diode 90a and transister 90b, are connected to drain off any voltage in excess of +7.8 volts from comparator 88, in a manner similar to that of a Zener diode; to prevent damage to lamp 45.

In the present invention, five filters are mounted in the filter wheel 48 having frequency ranges of 340; 450; 504; 540 and 590 nanometers, respectively. When the switch 86 is closed by insertion of a cuvette into well 30, and transister 91 is turned "on" there is no change in the operation just described unless the chemical analysis is one of those which require the use of the 340 nm. filter. In that case the output of comparator 88 will be higher than plus 5 volts. Since one of the inputs to comparator 92 is supplied with minus 5 volts from the resistance tap 93, the output of comparator 92 will be minus 12 volts which will be drawn to the ground by diode 94 resulting in a zero volt signal at one input to NOR gate 95. The other input, from the collector of transister 91 also being zero, the "one shot" circuit comprising gates 96a and 96b will generate a pulse for approximately 3 minutes. Since one input at gate 97 is already zero, the pulse at the other input will turn gate 97 "high" with the result that the output of gate 97 will be "low" for the duration of the 3-minute pulse. During this time, transister 98 is non-conductive and an increase over the normal voltage will be supplied to lamp 45 to compensate for the increased opacity of the 349 nm. filter. At the end of the 3-minute pulse period, the circuit returns to its standby condition of reduced voltage to conserve the life of the lamp filament.

What is claimed is:

1. In a direct reading digital colorimeter for performing a plurality of chemical constituent concentration analyses of liquid samples irradiated by light of preselected wavelengths of the type wherein a console contains a light source, filter means for isolating selectively a plurality of frequency ranges emitted by said source for irradiating a sample inserted in a cuvette well means provided in said console, sensing means including digital readout means and analog-to-digital computing circuit means controlling said readout means in response to the intensity of light received by the sensing means from a sample irradiated by a particular one of said frequency ranges to provide a direct digital readout of the constituent concentration of a particular sample, the improvement comprising;

switching means comprising a plurality of user manually operable elements for individually adjusting electrical values of components of said computing circuit means and for individually selecting ranges of slope of said filter means for providing a plurality of particular chemical analyses, and;

at least one other user operable switching means independent of said first mentioned manually operable elements comprising a single manually operable element pre-programmed to adjust said electrical values and a range of slope for conducting at least one particular chemical analysis.

2. The colorimeter defined in claim 1, wherein there is additionally provided means to provide a readout of prothrombin time when a blood sample is inserted in said well means.

3. The colorimeter defined in claim 2, wherein a separate light source, sensing means and readout means is provided for said prothrombin time analysis, whereby a prothrombin time test may be conducted simultaneously with a chemical analysis.

4. The colorimeter defined in claims 2 or 3, wherein said first mentioned manually operable elements comprise a plurality of controls rotatably mounted on said console and said least mentioned manually operable other element comprises at least one pushbutton switching means mounted on said console.

5. The colorimeter defined in any one claims of 1, 2 or 3, wherein said console is also provided with at least one temperature controlled well for a cuvette.

6. The colorimeter defined in claim 4, wherein said console is provided with at least two temperature controlled wells for sample cuvettes.

7. In a direct reading digital colorimeter for performing a plurality of chemical constituent concentration analyses and for performing a prothrombin time test of liquid samples irradiated by light of preselected wavelengths of the type wherein a console contains a light source, filter means for isolating selectively a plurality of frequency ranges emitted by said source for irradiating a sample inserted in a cuvette well means provided in said console, sensing means including digital readout means and analog-to-digital computing circuit means controlling said readout means in response to the intensity of light received by the sensing means for a sample irradiated by a particular one of said frequency ranges to provide a direct digital readout of the constituent concentration or the prothrombin time of a particular sample, the improvement comprising;

switching means comprising a plurality of manually operable elements for adjusting electrical values of components of said computing circuit means and for selecting ranges of frequencies of said filter means for providing a particular one of a plurality of chemical analyses, or said prothrombin time test.

separate wells for a chemical analysis cuvette and for a prothrombin time test cuvette;

sensing means responsive concurrently to light from a sample in each well, and;

separate readout means on said console responsive to said sensing means to display concurrent readouts of a chemical analysis and a prothrombin time test.

8. The colorimeter defined in claim 7, wherein said computing circuit means includes timing circuit means for displaying elapsed time on one of said readout means, and said console includes manually operable switching means for initiating operation of said timing circuit means independently of the conduct of a prothrombin time test.

9. The colorimeter defined in claim 8, wherein said switching means includes manually operable switching means for setting the length of elapsed time to be displayed and to energize an audible alarm at the end of said elapsed time.

10. The colorimeter defined in claim 7, wherein said console is also provided with at least two temperature controlled wells for concurrently receiving a chemical analysis cuvette and a prothrombin time cuvette.

* * * * *